(12) United States Patent
Burnham et al.

(10) Patent No.: US 7,957,917 B2
(45) Date of Patent: Jun. 7, 2011

(54) COPPER CONTAMINATION DETECTION METHOD AND SYSTEM FOR MONITORING COPPER CONTAMINATION

(75) Inventors: Jay Sanford Burnham, Fletcher, VT (US); Joseph Kerry Vaughn Comeau, Essex Junction, VT (US); Leslie Peter Crane, Williston, VT (US); James Randall Elliott, Richmond, VT (US); Scott Alan Estes, Essex Junction, VT (US); James Spiros Nakos, Essex Junction, VT (US); Eric Jeffrey White, Charlotte, VT (US)

(73) Assignee: International Business Machines Corporation, Armonk, NY (US)

( * ) Notice: Subject to any disclaimer, the term of this patent is extended or adjusted under 35 U.S.C. 154(b) by 478 days.

(21) Appl. No.: 11/863,623

(22) Filed: Sep. 28, 2007

(65) Prior Publication Data

US 2009/0088984 A1    Apr. 2, 2009

(51) Int. Cl.
    *G01N 30/04*    (2006.01)
(52) U.S. Cl. .............. 702/25; 702/22; 702/23; 702/188
(58) Field of Classification Search ............... 702/19, 702/25, 28, 82, 116, 117, 127, 179, 183; 324/750; 356/244; 438/14, 471
    See application file for complete search history.

(56) References Cited

U.S. PATENT DOCUMENTS

| | | | | |
|---|---|---|---|---|
| 6,607,927 B2 * | 8/2003 | Ramappa et al. | ............... | 438/14 |
| 6,737,221 B2 * | 5/2004 | Futase et al. | ................... | 430/311 |
| 7,141,992 B2 * | 11/2006 | Ohno et al. | .................... | 324/750 |
| 2002/0180986 A1 | 12/2002 | Nikoonahad et al. | | |
| 2002/0182760 A1 | 12/2002 | Wack et al. | | |
| 2003/0064533 A1 | 4/2003 | Ramappa et al. | | |
| 2003/0104680 A1 * | 6/2003 | Stefanescu et al. | ........... | 438/471 |
| 2005/0250297 A1 | 11/2005 | Shive et al. | | |

OTHER PUBLICATIONS

Boehringer et al.; Improved copper detection in hydrofluoric acid by recombination lifetime measurements on dedicated silicon substrates; 2002 American Institute of Physics; Applied Physics Letters, vol. 80, No. 3; Jan. 21, 2002; pp. 527-529.
Office Action (Mail Date Apr. 12, 2010) for U.S. Appl. No. 11/863,502, filed Sep. 28, 2007.
Notice of Allowance (Mail Date Oct. 4, 2010) for U.S. Appl. No. 11/863,502, filed Sep. 28, 2007.
U.S. Appl. No. 12/973,062, filed Dec. 20, 2010.

* cited by examiner

*Primary Examiner* — Mohamed Charioui
*Assistant Examiner* — Felix E Suarez
(74) *Attorney, Agent, or Firm* — Schmeiser, Olsen & Watt; David Cain

(57) ABSTRACT

A computer system. The computer system including a processor and memory unit coupled to the processor, the memory unit containing instructions that when executed by the processor implement a method for monitoring a solution in a tank used to fabricate integrated circuits, the method comprising the computer implemented steps of: (a) collecting data indicating of an amount of copper in a region of a substrate of a monitor, the monitor comprising an N-type region in a silicon substrate, the region abutting a top surface of the substrate, the monitor having been submerged in the solution for a preset time; (b) comparing the data to a specification for copper content of the solution; (c) if the data indicates a copper content exceeds a limit of the specification for copper, indicating a corrective action is required to prevent copper contamination of the integrated circuits; and (d) repeating steps (a) through (c) periodically.

18 Claims, 6 Drawing Sheets

COPPER CONTAMINATION DETECTION METHOD AND SYSTEM FOR MONITORING COPPER CONTAMINATION

RELATED APPLICATIONS

This Application is related to application Ser. No. 11/863,502 filed on Sep. 28, 2007 entitled "COPPER CONTAMINATION DETECTION METHOD AND SYSTEM FOR MONITORING COPPER CONTAMINATION".

FIELD OF THE INVENTION

The present invention relates to the field of integrated circuit fabrication; more specifically, it relates to a method for monitoring copper contamination in an integrated circuit fabrication facility and a system for monitoring copper contamination in an integrated circuit fabrication facility.

BACKGROUND OF THE INVENTION

Modern integrated circuits are fabricated with copper interconnection wiring. Wet processing tanks in the integrated circuit fabrication can be contaminated with copper, causing yield loss and reliability concerns. Accordingly, there exists a need in the art for methods and systems for monitoring copper contamination of solution in wet processing tanks in integrated circuit manufacturing facilities.

SUMMARY OF THE INVENTION

A first aspect of the present invention is a computer system comprising a processor, an address/data bus coupled to the processor, and a computer-readable memory unit coupled to communicate with the processor, the memory unit containing instructions that when executed by the processor implement a method for monitoring a solution in a tank of a processing tool used to fabricate integrated circuits, the method comprising the computer implemented steps of: (a) collecting data indicating of an amount of copper in a region of a substrate of a monitor, the monitor comprising an N-type region in a single-crystal silicon substrate, the region abutting a top surface of the substrate, the monitor having been submerged in the solution for a preset duration of time; (b) comparing the data to a specification for copper content of the solution; (c) if the data indicates a copper content exceeds a limit of the specification for copper, indicating a corrective action is required to prevent copper contamination of the integrated circuits; and (d) repeating steps (a) through (c) periodically.

A second aspect of the present invention is the computer system of the first aspect, the method further including the step of: between (b) and (c) determining a copper concentration of the solution based on the amount of copper.

A third aspect of the present invention is the computer system of the second aspect, the method further including the step of: displaying the copper concentration on a computer screen.

A fourth aspect of the present invention is the computer system of the second aspect, the method further including the step of: storing the copper concentration on a storage media.

A fifth aspect of the present invention is the computer system of the fourth aspect, the method further including the step of: generating and displaying a control chart of the copper concentration over time.

A sixth aspect of the present invention is the computer system of the first aspect, the method further including the step of: determining a copper concentration of the solution based on the data and an empirically derived curve, table or formula derived from measuring amounts of copper in monitor wafers submerged, for the present duration of time, in respective aqueous solutions having known and different copper concentrations.

A seventh aspect of the present invention is the computer system of the first aspect, wherein the data includes Total Internal Reflected X-Ray Fluorescence copper content data, Secondary Ion Mass Spectroscopy copper content data, Time of Flight SIMS copper content data, Energy Dispersive X-Ray Fluorescence copper content data, Auger Spectroscopy copper content data or X-Ray Photo-electron Spectroscopy copper content data.

An eighth aspect of the present invention is the computer system of the first aspect, the method further including the step of: based on the data, selecting an instruction from a list of instructions; and displaying the instruction on a computer screen.

A ninth aspect of the present invention is the computer system of the eighth aspect, wherein the instruction is selected from the group consisting of (i) an instruction to shut down the tank of the processing tool containing the solution, (ii) an instruction to limit types of product wafers allowed in the tank, (iii) an instruction to restrict fabrication levels of product wafers allowed in the tank, (iv) an instruction to limit a number of product wafers that can be processed before shutting down the tank, and (v) an instruction to shut down the tank, drain the solution from the tank, clean the tank, and refill the tank with fresh solution.

A tenth aspect of the present invention is a computer system comprising a processor, an address/data bus coupled to the processor, and a computer-readable memory unit coupled to communicate with the processor, the memory unit containing instructions that when executed by the processor implement a method for monitoring a solution in a tank of a processing tool used to fabricate integrated circuits, the method comprising the computer implemented steps of: (a) collecting data indicating of an amount of copper in a region of a substrate of a monitor, the monitor comprising an N-type region in a single-crystal silicon substrate, the region abutting a top surface of the substrate, the monitor having been submerged in the solution for a preset duration of time; (b) comparing the data to a specification for copper content of the region of the substrate; (c) if the data indicates a copper content exceeds a limit of the specification for copper, indicating a corrective action is required to prevent copper contamination of the integrated circuits; and (d) repeating steps (a) through (c) periodically.

BRIEF DESCRIPTION OF THE DRAWINGS

The features of the invention are set forth in the appended claims. The invention itself, however, will be best understood by reference to the following detailed description of an illustrative embodiment when read in conjunction with the accompanying drawings, wherein:

DETAILED DESCRIPTION OF THE INVENTION

Integrated circuits are fabricated in silicon layers of disc shaped semiconductor substrates often referred to as wafers. These wafers can have diameters of, to give a few examples, of 125 mm, 200 mm and 300 mm. The fabrication of integrated circuits requires frequent dipping of wafers into tanks containing various neutral, acidic (e.g., hydrofluoric, nitric, sulfuric, phosphoric and acetic) and basic (potassium hydroxide, tetramethylammonium hydroxide, ammonium hydroxide) aqueous wafer cleaning solutions, aqueous wafer etching solutions, aqueous photoresist developing solutions and aqueous photoresist removal solutions. Copper dissolved in these solutions can be adsorbed on the surface of N-type silicon when the surface concentration of N-type dopant (e.g., arsenic, phosphorous) exceeds a threshold value (e.g., about 1 E13 atm/cm$^2$ or higher). The higher the N-type dopant surface concentration, the more copper will be adsorbed on the surface.

Figure 1A:
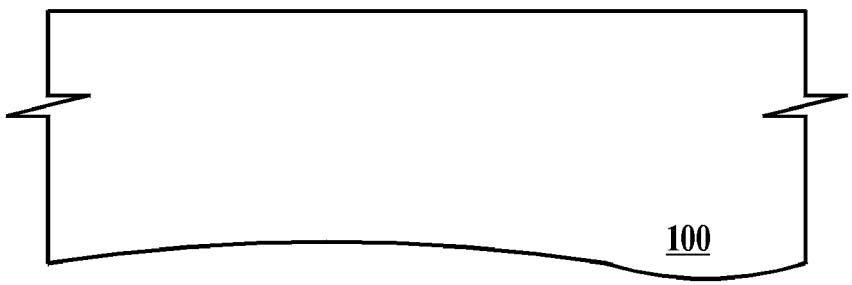
FIGS. 1A through 1D are cross-sectional drawings illustrating preparation of a monitor wafer according to embodiments of the present invention.

FIGS. 1A through 1D are cross-sectional drawings illustrating preparation of a monitor wafer according to embodiments of the present invention. In FIG. 1A a lightly (having a resistivity between about 10 ohm-cm and about 20 ohm-cm P-doped single-crystal silicon substrate 100 is provided. Substrate 100 may be cleaned, in one example, by immersion an aqueous solution of ammonia and hydrogen peroxide followed by immersion an aqueous solution of hydrogen chloride and hydrogen peroxide. Alternatively, substrate 100 may be lightly doped N-type (having a resistivity between about 50 ohm-cm and about 0.7 ohm-cm. Alternatively, substrate 100, may comprise upper and lower single-crystal silicon layers separated by a buried oxide (BOX) layer, commonly known as a silicon-on-insulator (SOI) substrate. Substrate 100 is advantageously a wafer having the same dimensions (diameter and thickness) of wafers on which integrated circuits processed through the tanks to be monitored. This allows normal wafer handling mechanisms and wafer routing procedures to be used.

Figure 1B:
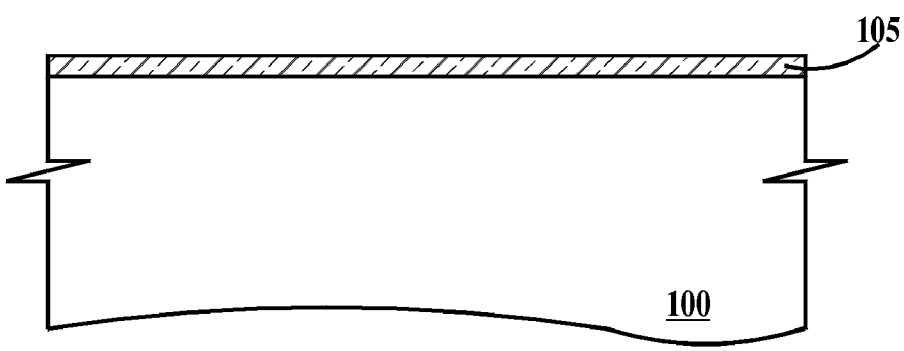
Figure 1C:
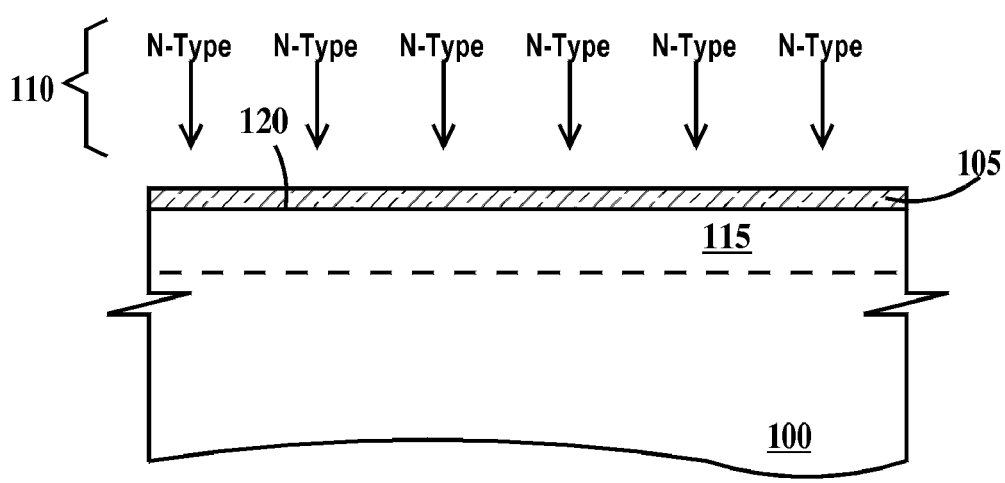

In FIG. 1B, an optional thermal silicon dioxide layer 105 is grown on by thermal oxidation (e.g., by oxidation at a temperature of about 500° C. or higher in oxygen in a furnace for about 30 minutes or by oxidation at a temperature of about 900° C. in oxygen for 5 seconds in a rapid-thermal-anneal (RTA) tool) of the surfaces of substrate 100. In one example, silicon dioxide layer is between about 0.4 nm and about 20 nm thick. Silicon dioxide layer 105 protects substrate 100 from contamination. Silicon dioxide layer 105 also helps to control the dopant profile generated by the steps described infra in relation to FIG. 1C.

In FIG. 1, an N-type ion implantation 110 is performed followed by an annealing step (e.g., at a temperature of about 500° C. or higher in an inert atmosphere in a furnace for about 30 minutes or at a temperature of about 900° C. in an inert atmosphere for 5 seconds in a RTA tool) to form an N-doped silicon region 115 in substrate 110. N-type ion implantation 110 may implant a phosphorus species or an arsenic species or a combination of both and arsenic and phosphorus species. N-doped region 115 extends from top surface 120 of substrate 100 a depth into the substrate determined by the thickness of silicon dioxide layer 105, the ion implantation dose, the ion implantation accelerating voltage, the ion implantation species and the anneal time and temperature. In one example, the ion implantation accelerating voltage is between about 2 KeV and about 25 KeV. In one example, the ion implantation dose of N-dopant species is between about 4 E13 atm/cm$^2$ an about 1 E16 atm/cm$^2$. The higher the concentration, the higher the sensitivity of the monitor to copper, but above an ion implantation does about 1 E116 atm/cm$^2$ cost and time of the ion implantation may be a factor. The dopant ion implantation dose and energy should be selected to repeatably provide a copper measuring sensitivity in the range of copper concentrations expected to be found in the solutions to be monitored.

At this point fabrication of the monitor wafer may be terminated and the monitor wafer stored for future use. Alternatively, the process described infra in reference to FIG. 1D may be performed.

Figure 1D:
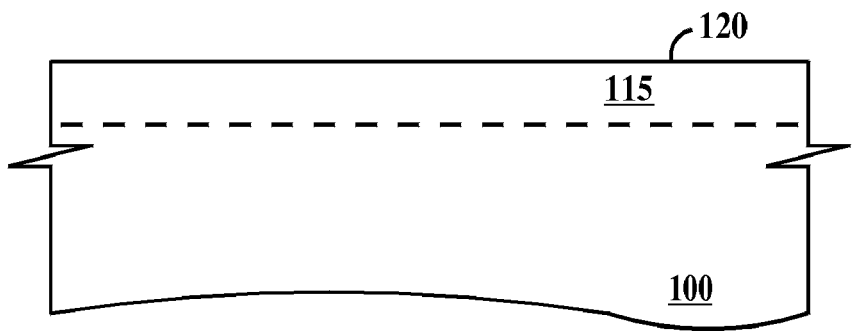

In FIG. 1D, thermal oxide layer 105 (see FIG. 1C) is removed. In one example, by etching in an aqueous hydrofluoric acid solution followed by a water rinse. The hydrofluoric acid solution may include ethylene glycol or ammonium fluoride. Other $SiO_2$ etchants may be used. A very thin native oxide layer (about 0.1 nm or less will form after rinsing). At this point the wafers may be stored. If no silicon oxide layer 105 was formed, then this step may be eliminated. A post anneal clean, similar to that described supra in reference to FIG. 1A may be performed.

Figure 2:
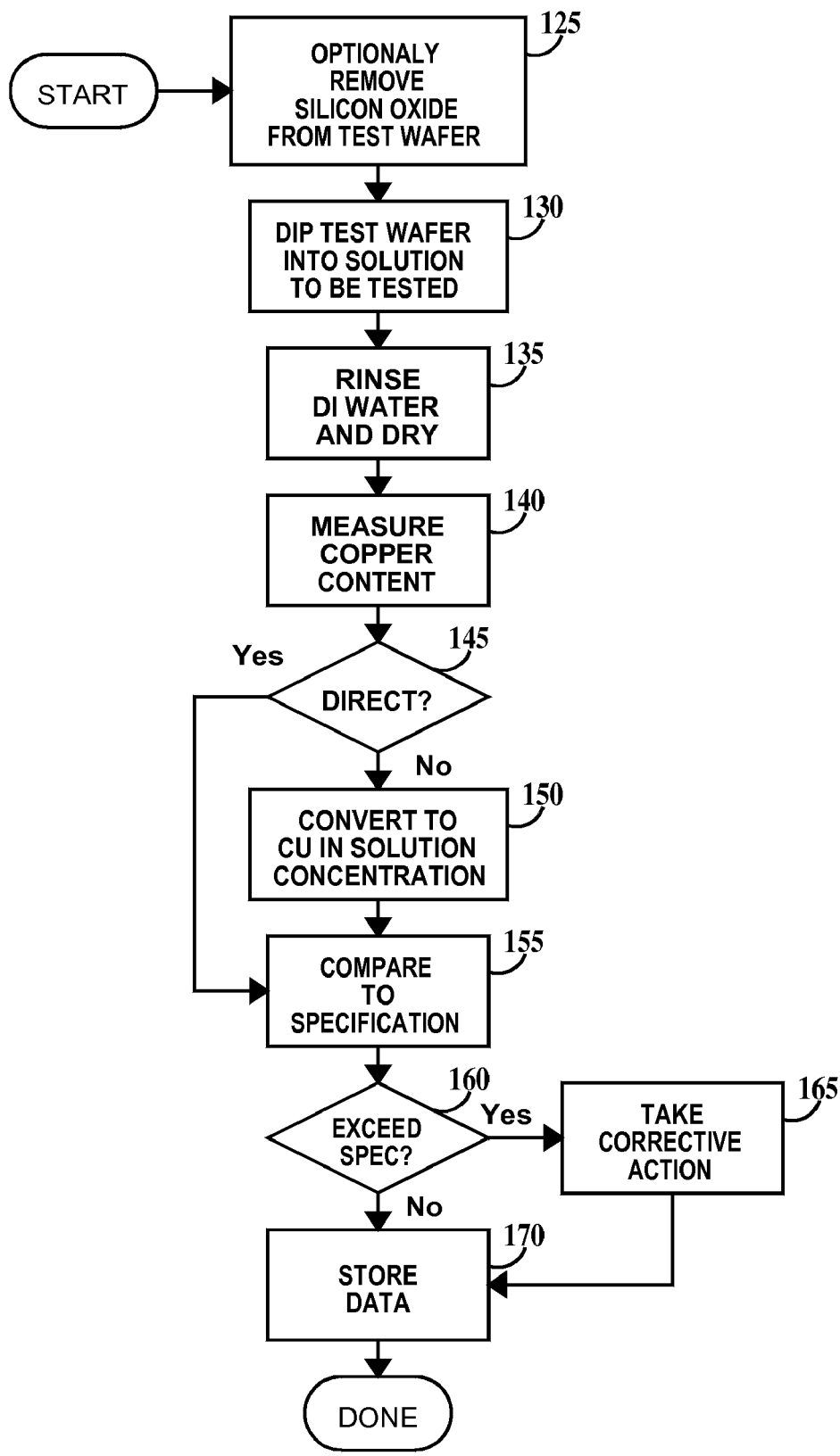
FIG. 2 is a flowchart for testing for copper contamination according to embodiments of the present invention.
Figure 3A:
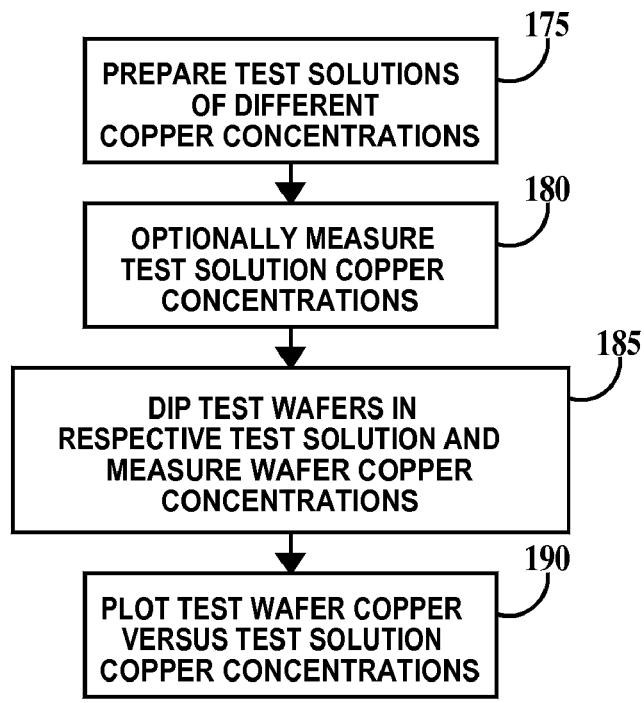
FIGS. 3A and 3B are flowcharts illustrating calibration of measurement procedures according to embodiments of the present invention.
Figure 3B:
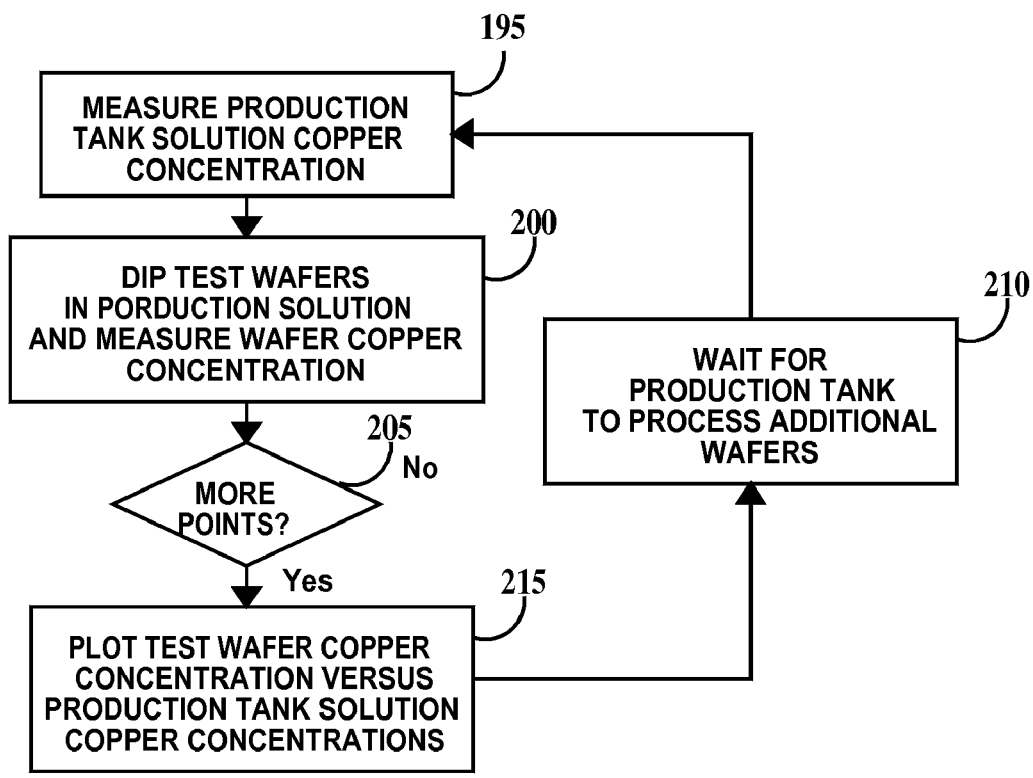

In the steps of FIGS. 2, 3A and 3B that follow, either a whole monitor wafer may be used or a portion of a monitor wafer. While the method will be described using whole wafers, it should be understood that whole wafers may be broken into multiple pieces and these pieces used instead of whole wafers. The use of whole wafers allows the use of the normal wafer handling equipment of automated processing tools. The use of pieces of monitor wafers reduces the cost preparing monitor wafers.

FIG. 2 is a flowchart for testing for copper contamination according to embodiments of the present invention. The method of monitoring for copper contamination starts by selecting a monitor wafer prepared as described supra. Step 125 is optional and is performed if the solution in the tank to be tested will not remove $SiO_2$ (e.g., does not contain fluorine ions) or will remove $SiO_2$ at such a slow rate as to effect the measurement or impact manufacturing schedules, then the monitor wafer is prepared by removing the $SiO_2$ layer (either thermal oxide layer 105 of FIG. 1C or the native oxide formed after removal of the thermal oxide layer as described supra). Removal of $SiO_2$ may be accomplished, for example, by etching in an aqueous hydrofluoric acid solution followed by a water rinse. The hydrofluoric acid solution may include ethylene glycol or ammonium fluoride. Other $SiO_2$ etchants may be used. If the solution of the tank to be tested will remove $SiO_2$, then step 125 may be skipped. The $SiO_2$ is removed because copper ions are not adsorbed on $SiO_2$ surfaces.

In step 130 the monitor wafer is dipped into the solution of the tank to be tested for a preset duration of time. After the preset time expires, in step 135, the monitor wafer is removed from the tank, rinsed in deionized water and dried. Then in step 140 the copper content of the monitor wafer is measured.

There are many methods and tools that may be used to measure the copper content of thin regions of the surface of the monitor wafer. Examples include, but are not limited to Total Internal Reflected X-Ray Fluorescence (TXFR), Secondary Ion Mass Spectroscopy (SIMS), Time of Flight SIMS (TOFSIMS), Energy Dispersive X-Ray Fluorescence (EDX), Auger Spectroscopy and X-Ray Photo-electron Spectroscopy (XPS).

In Step 145, a decision is made to compare the resultant copper measurement directly to an amount of copper allowed monitor wafer specification or convert the measurement to a copper concentration (e.g., parts per billion PPB) and compare to a copper concentration allowed in the solution specification. If conversion to solution concentration is required the method proceeds to step 150, otherwise the method proceeds to step 155.

If the comparison is to be based on a copper in solution concentration then in step 150 the measurement obtained in step 145 is converted, for example by use of a conversion graph (see FIG. 4), a conversion formula or a look-up table. In reality all three conversion methods are procedures applied to the same data. It should be understood that there are two types of copper in solution concentration conversions that can be performed and which are described infra in relation to FIGS. 3A, 3B and 4.

In step, 155, comparison to a specification indicating either a measured copper value or of a converted to copper in solution concentration value is performed. In one example the comparison is a simple look-up table procedure or a calculation based on a conversion formula. In one example, this is a control chart procedure, where results of values over time are charted, various statistical analysis are performed and control limits applied.

In step, 160, it is determined if the copper specification has been exceeded. If the copper specification has been exceeded, then the method proceeds to step 165, otherwise the method proceeds to step 170. In step 170, corrective action is taken. Corrective actions can include, for example, shutting down the tank and changing the solution, limiting the type of product wafers allowed in a particular tank (e.g., by part number), restricting the fabrication level of the product wafers allowed in the tank (e.g., to levels less sensitive or insensitive to copper contamination), limiting the number of product wafers that can be processed before shutting the tank down, and shutting the tank down, draining the contaminated solution, cleaning the tank, and refilling with fresh solution.

In step 170, the copper measurement and/or converted copper in solution value is labeled by date/time and tank ID and saved, and the method is complete.

FIGS. 3A and 3B are flowcharts illustrating calibration of measurement procedures according to embodiments of the present invention. Referring to FIG. 3A, in step 175 several solutions having known copper concentrations are prepared. These solutions may contain a fluorine based etchant. In step 180, the concentration of copper in the various test solutions is optionally verified by conventional quantitative copper analysis techniques. In step 185, monitor wafers are dipped into the different test solutions for a preset duration of time. The same preset duration of time is used for each solution. A different monitor wafer is dipped into each test solution. After rinsing and drying, the copper concentrations of the monitor wafers are measured using the analysis technique described in step 140 of FIG. 2 (e.g., TXFR, etc). In step 190, the copper concentrations measured in step 185 are plotted versus the copper concentrations from step 175 or 180 (see curve 225 of FIG. 4). The data points obtained may also be entered into a database and a conversion formula calculated from the data points.

Referring to FIG. 3B, step 195 the copper concentrations of a solution in a production tank is measured by conventional quantitative copper analysis techniques. In step 200, monitor wafers are dipped into the solution of the production tank for the same preset duration of time used in step 185 of FIG. 3A. After rinsing and drying, the copper concentrations of the monitor wafer is measured using the analysis technique used in step 185 of FIG. 3A (e.g., TXFR, etc). In step 205, it is determined if more data point are required. If more data points are required, then in step 210 enough time is allowed to pass to ensure a significant number (e.g., several hundred) production wafers have been processed though the solution of the production tank before proceeding to step 195. Otherwise the method proceeds to step 215. In step 215, the copper concentrations measured in step 200 are plotted versus the copper concentrations from step 195 (see curve 220 of FIG. 4). The data points obtained may also be entered into a database and a conversion formula calculated from the data points.

Figure 4:
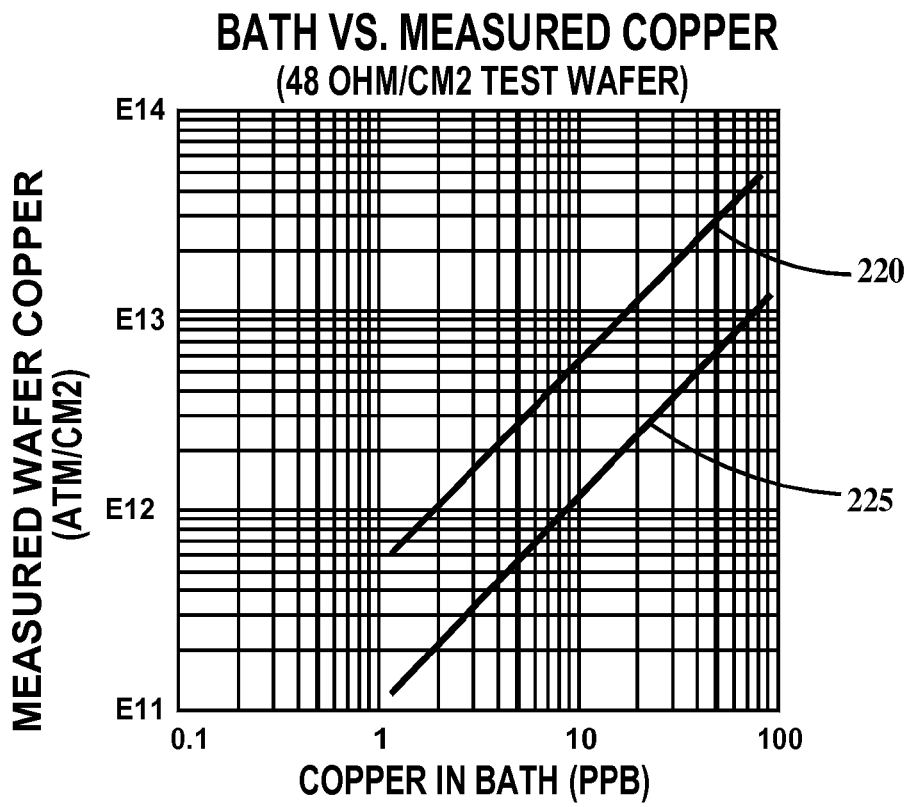
FIG. 4 is a log-log plot of known (or measured) copper concentration of a solution in a tank versus wafer copper surface concentration of wafers soaked in the solution of the tank.

FIG. 4 is a log-log plot of known (or measured) copper concentration of a solution in a tank versus wafer copper surface concentration of wafers soaked in the solution of the tank. The monitor wafers used to prepare curves 220 and 225 were processed by implanting a dose of $1E16$ atm/cm$^2$ arsenic at 2 KeV into a P type substrate and then RTA at 900° C. for 5 minutes. The sheet resistance was measured at 48 ohm/cm$^2$. In FIG. 4, curve 225 is based on test solutions prepared in control tanks and curve 225 is based on solutions in production tanks. The wafer concentrations were obtained using TXFR. From FIG. 4 it can be seen that both curves 220 and 225 are linear in a log-log scale. From FIG. 4 it can be seen that there is a constant offset between curve 220 and curve 225, with curve 220 (production tank solution) reporting more copper in solution than curve 225 (test tank solution) for the same TXRF value. This is thought to occur because of additional chemicals (e.g., dissolved Si) in the production tank enhancing monitor wafer copper adsorption or a difference in fluorine ion content between the production and test solutions. The TXFR measurement reports less copper in the production bath than is actually present. Therefore, step 150 of FIG. 2 can use either of curve 220 or 225 (or formulas or look-up tables based on the data points of curves 220 and 225) for conversion.

Figure 5:
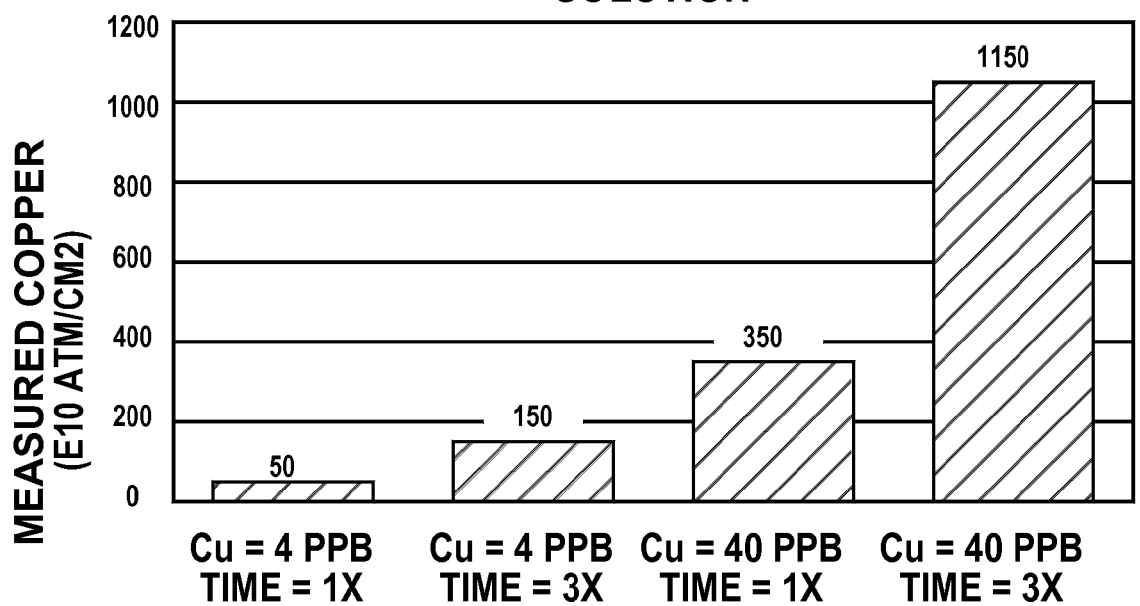
FIG. 5 is a plot of known copper concentrations of solutions in control tanks versus wafer copper surface concentration by time of soak.

FIG. 5 is a plot of known copper concentrations of solutions in control tanks versus wafer copper surface concentration by time of soak. The wafer concentrations were obtained using TXFR. FIG. 5 shows that copper adsorption by the monitor wafers is linear over time over a wide (e.g. 4 ppb to 40 ppb) range of copper in solution concentrations. The number above each histogram are approximate.

Figure 6:
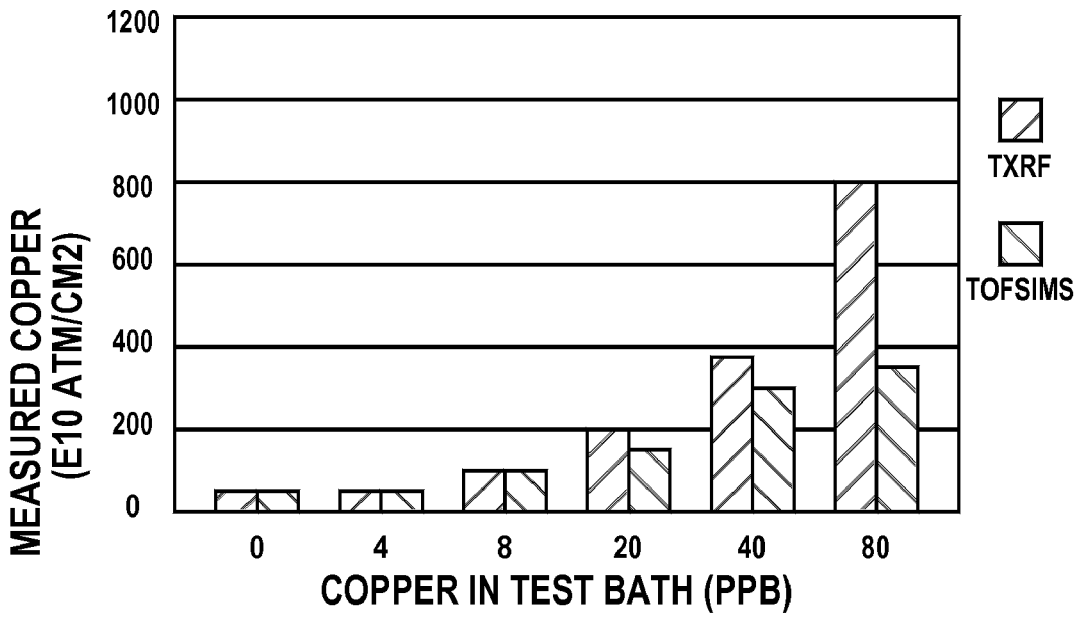
FIG. 6 is a plot of known copper concentration of a solution in a control tank versus wafer copper surface concentrations obtained by two wafer measurement techniques at a first dopant level.

FIG. 6 is a plot of known copper concentration of a solution in a control tank versus wafer copper surface concentrations obtained by two wafer measurement techniques at a first dopant level. In FIG. 6, measurements were made on similar monitor wafer using TXRF and TOFSIMS. The monitor wafers used to prepare FIG. 6 were processed by implanting a dose of $1E16$ atm/cm$^2$ arsenic at 2 KeV into a P type substrate and then RTA at 900° C. for 5 minutes.

Figure 7:
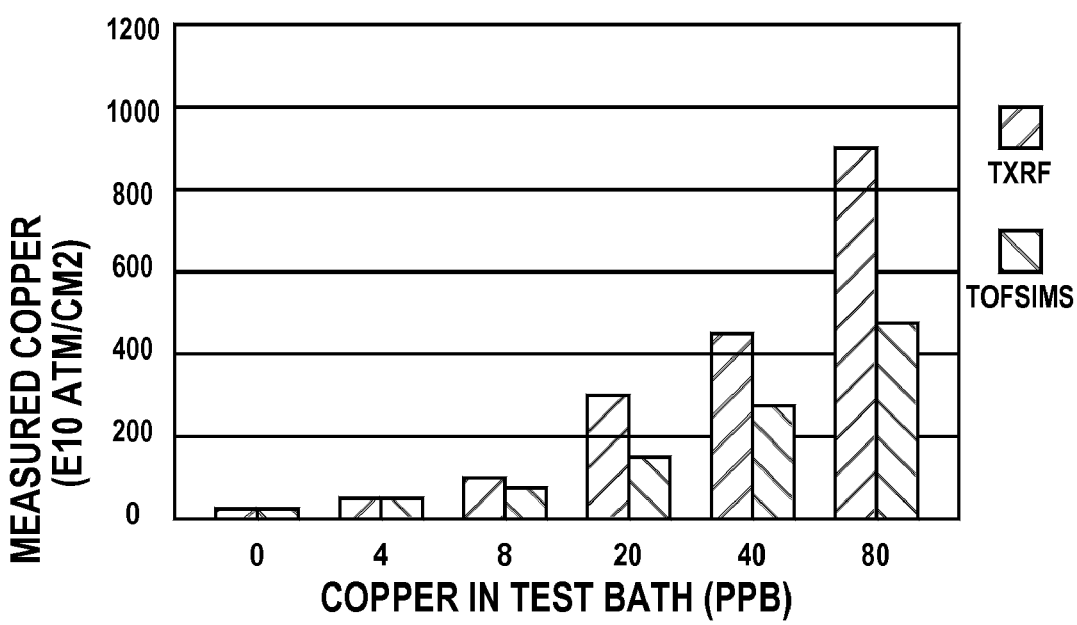
FIG. 7 is a plot of known copper concentration of a solution in a control tank versus wafer copper surface concentrations obtained by two wafer measurement techniques at a second dopant level.

FIG. 7 is a plot of known copper concentration of a solution in a control tank versus wafer copper surface concentrations obtained by two wafer measurement techniques at a second dopant level. In FIG. 6, measurements were made on similar monitor wafer using TXRF and TOFSIMS. The monitor wafers used to prepare FIG. 6 were processed by implanting a dose of 5E15 atm/cm$^2$ arsenic at 2 KeV into a P type substrate and then RTA at 900° C. for 5 minutes.

Comparing FIGS. 6 and 7, the two methods (TXRF and TOFSIMS) generate different values, but track very well.

TXRF reports about the same copper solution concentrations for both dopant levels, while TOFSIMS reports about the same copper solution concentrations for both dopant levels except at 80 ppb and TXRF and TOFSIMS generally track, except for 80 ppb. To ensure the highest accuracy, calibration should be performed using the same dopant level monitor wafers and same wafer copper concentration measurement technique.

Figure 8:
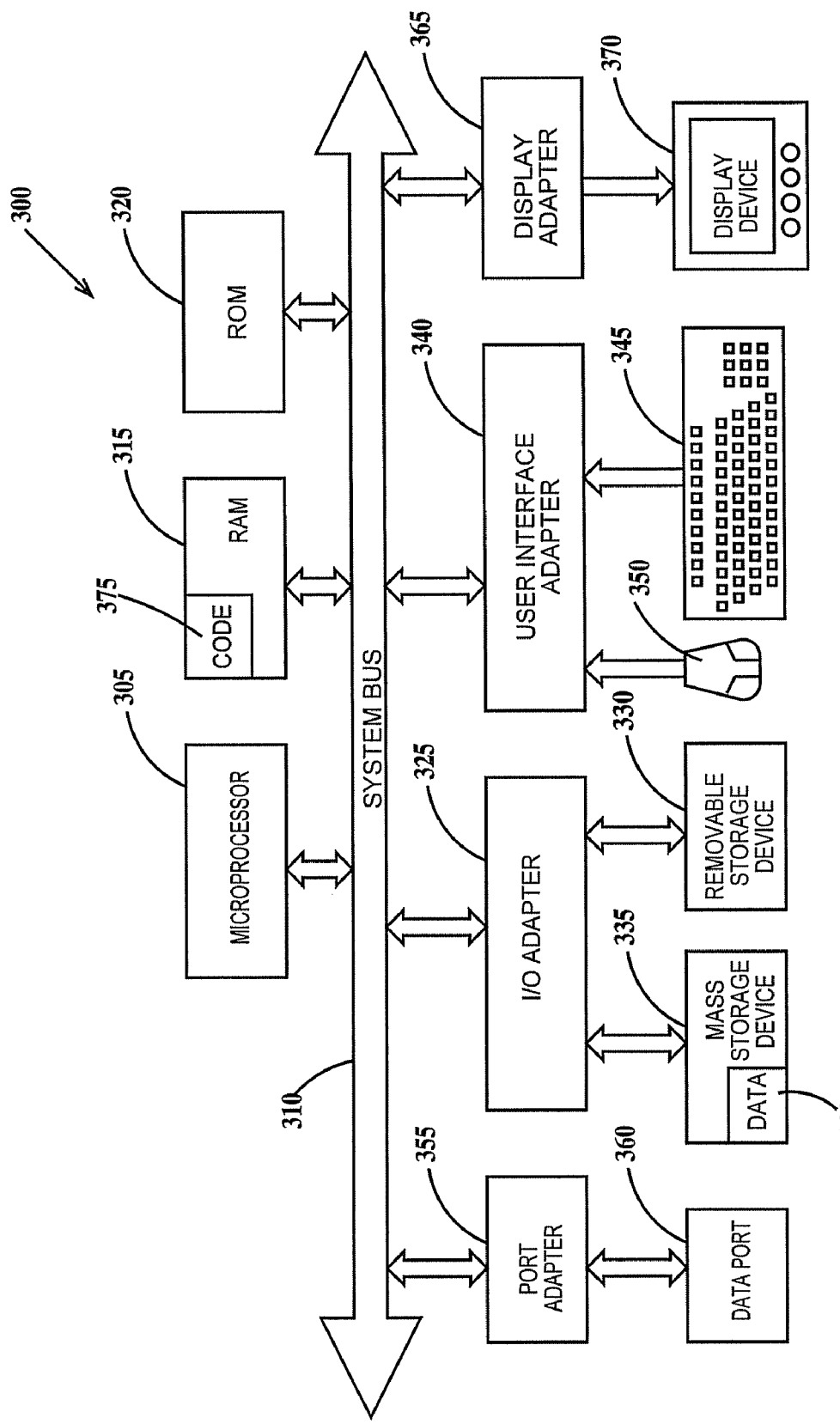
FIG. 8 is a schematic block diagram of a general-purpose computer for practicing the embodiments of the present invention.

FIG. 8 is a schematic block diagram of a general-purpose computer for practicing the embodiments of the present invention. In FIG. 8, computer system 300 has at least one microprocessor or central processing unit (CPU) 305. CPU 305 is interconnected via a system bus 310 to a dynamic random access memory (DRAM) device 315 and a read-only memory (ROM) device 320, an input/output (I/O) adapter 325 for a connecting a removable data and/or program storage device 330 and a mass data and/or program storage device 335, a user interface adapter 340 for connecting a keyboard 335 and a mouse 350, a port adapter 355 for connecting a data port 360 and a display adapter 365 for connecting a display device 370.

Either of devices 315 and 320 includes contains the basic operating system for computer system 300. Removable data and/or program storage device 330 may be a magnetic media such as a floppy drive, a tape drive or a removable hard disk drive or optical media such as CD ROM or a digital video disc (DVD) or solid state memory such as ROM or DRAM or flash memory. Mass data and/or program storage device 335 may be a hard disk drive or an optical drive. In addition to keyboard 335 and mouse 350, other user input devices such as trackballs, writing tablets, pressure pads, microphones, light pens and position-sensing screen displays may be connected to user interface 330. Examples of display devices include cathode-ray tubes (CRT) and liquid crystal displays (LCD).

One of devices 315, 320, 330 or 335 includes a computer code 375 (illustrated by way of example in device 315), which is a computer program that comprises computer-executable instructions. Computer code 375 includes an algorithm for generating calibration and conversion curves, tables or equation for copper in solution to copper adsorbed on a monitor wafer surfaces as well as for monitoring copper contamination in production wet processing tanks (e.g. the algorithm of FIGS. 2, 3A, 3B and curves of FIG. 4). CPU 305 executes computer code 375. Additional activities implemented on the computer system 300 include generating history or trend charts from periodic monitor measurements and performing statistical analysis on the periodic data. Any of devices 315, 320, 330 or 335 may include input data 380 (illustrated by way of example in device 335) required by computer code 375. Display device 370 displays output from computer code 375.

Any or all of devices 315, 320, 330 and 335 (or one or more additional memory devices not shown in FIG. 3) may be used as a computer usable medium (or a computer readable medium or a program storage device) having a computer readable program embodied therein and/or having other data stored therein, wherein the computer readable program comprises computer code 375. Generally, a computer program product (or, alternatively, an article of manufacture) of the computer system 300 may comprise the computer usable medium (or the program storage device).

Computer system 300 can indicate corrective actions to take by selecting an instruction from a list of instructions based on monitor wafer copper content measurements and displaying the instruction on, for example, display device 370. The instructions would correlate to the corrective actions listed supra and would be (for example) selected from the group consisting of (i) an instruction to shut down the tank of the processing tool containing the solution, (ii) an instruction to limit types of product wafers allowed in the tank, (iii) an instruction to restrict fabrication levels of product wafers allowed in the tank, (iv) an instruction to limit a number of product wafers that can be processed before shutting down the tank, and (v) an instruction to shut down the tank, drain the solution from the tank, clean the tank, and refill the tank with fresh solution.

Thus the present invention discloses a process for supporting computer infrastructure, integrating, hosting, maintaining, and deploying computer-readable code into the computer system 300, wherein the code in combination with the computer system 300 is capable of performing a method for monitoring copper contamination in wet processing tanks of integrated circuit fabrication facilities.

Thus, the embodiments of the present invention provide methods and systems for monitoring copper contamination of solutions in wet processing tanks in integrated circuit manufacturing facilities.

The description of the embodiments of the present invention is given above for the understanding of the present invention. It will be understood that the invention is not limited to the particular embodiments described herein, but is capable of various modifications, rearrangements and substitutions as will now become apparent to those skilled in the art without departing from the scope of the invention. For example, the present invention may be used to monitor spray processing tools where the solution is continuously collected and reused. Therefore, it is intended that the following claims cover all such modifications and changes as fall within the true spirit and scope of the invention.

What is claimed is:

1. A computer system comprising, a processor, a computer-readable storage device coupled to said processor, said storage device containing program code configured to be executed by said processor via said memory to implement a method for monitoring a solution in a tank of a processing tool used to fabricate integrated circuits, said method comprising:

(a) receiving data indicating of an amount of copper in a region of a substrate of a monitor, said monitor comprising an N-type region in a single-crystal silicon substrate, said region abutting a top surface of said substrate, said monitor having been submerged in said solution for a preset duration of time;

(b) converting said data indicating of said amount of copper in said region of said substrate of a monitor to data indicating an amount of copper in said solution and comparing said data indicating said amount of copper in said solution to a specification for copper content of said solution; and (c) if said data indicating an amount of copper in said solution exceeds a limit of said specification for the copper content, indicating a corrective action is required to prevent copper contamination of said integrated circuits.

2. The computer system of claim 1, the method further including the step of:
   determining a copper concentration of said solution based on said amount of copper in said region of said substrate.

3. The computer system of claim 2, the method further including the step of:
   displaying said copper concentration of said solution on a computer screen.

4. The computer system of claim 2, the method further including the step of:
   storing said copper concentration on a computer readable storage media.

5. The computer system of claim 4, the method further including the step of:
   generating and displaying a control chart of said copper concentration over time on a computer screen.

6. The computer system of claim 1, wherein said converting is based on an (i) empirically derived curve, (ii) a look-up table or (iii) an algorithm, said curve, table or algorithm derived from measuring amounts of copper in monitor wafers submerged, for said present duration of time, in respective aqueous solutions having known and different copper concentrations.

7. The computer system of claim 1, wherein said data includes Total Internal Reflected X-Ray Fluorescence copper content data, Secondary Ion Mass Spectroscopy copper content data, Time of Flight SIMS copper content data, Energy Dispersive X-Ray Fluorescence copper content data, Auger Spectroscopy copper content data or X-Ray Photo-electron Spectroscopy copper content data.

8. The computer system of claim 1, the method further including the step of:
   selecting an instruction for said corrective action from a list of instructions stored on said computer system; and
   displaying said instruction on a computer screen.

9. The computer system of claim 8, wherein said instruction is selected from the group consisting of (i) an instruction to shut down said tank of said processing tool containing said solution, (ii) an instruction to limit types of product wafers allowed in said tank, (iii) an instruction to restrict fabrication levels of product wafers allowed in said tank, (iv) an instruction to limit a number of product wafers that can be processed before shutting down said tank, and (v) an instruction to shut down said tank, drain said solution from said tank, clean said tank, and refill said tank with fresh solution.

10. The computer system of claim 1, the method further including the step of:
    (d) repeating steps (a) through (c) periodically.

11. A computer system comprising, a processor, a computer-readable storage device coupled to said processor, said storage device containing program code configured to be executed by said processor via said memory to implement a method for monitoring a solution in a tank of a processing tool used to fabricate integrated circuits, said method:
    (a) receiving data indicating of an amount of copper in a region of a substrate of a monitor, said monitor comprising an N-type region in a single-crystal silicon substrate, said region abutting a top surface of said substrate, said monitor having been submerged in said solution for a preset duration of time;
    (b) comparing said data to a specification for copper content of said region of said substrate; and
    (c) if said data indicates a copper content exceeds a limit of said specification for copper, indicating a corrective action is required to prevent copper contamination of said integrated circuits.

12. The computer system of claim 11, the method further including the step of:
    displaying said data on a computer screen.

13. The computer system of claim 11, the method further including the step of:
    storing said data on a non-transitory computer readable storage media.

14. The computer system of claim 11, the method further including the step of:
    generating and displaying a control chart of said data over time on a computer screen.

15. The computer system of claim 11, wherein said data includes Total Internal Reflected X-Ray Fluorescence copper content data, Secondary Ion Mass Spectroscopy copper content data, Time of Flight SIMS copper content data, Energy Dispersive X-Ray Fluorescence copper content data, Auger Spectroscopy copper content data or X-Ray Photo-electron Spectroscopy copper content data.

16. The computer system of claim 11, the method further including the step of:
    selecting an instruction for said corrective action from a list of instructions stored in computer system; and
    displaying said instruction on a computer screen.

17. The computer system of claim 16, wherein said instruction is selected from the group consisting of (i) an instruction to shut down said tank of said processing tool containing said solution, (ii) an instruction to limit types of product wafers allowed in said tank, (iii) an instruction to restrict fabrication levels of product wafers allowed in said tank, (iv) an instruction to limit a number of product wafers that can be processed before shutting down said tank, and (v) an instruction to shut down said tank, drain said solution from said tank, clean said tank, and refill said tank with fresh solution.

18. The computer system of claim 11, the method further including the step of:
    (d) repeating steps (a) through (c) periodically.

* * * * *